United States Patent [19]

Lee et al.

[11] Patent Number: 4,556,520

[45] Date of Patent: Dec. 3, 1985

[54] 2-NITRO(CYANO)PHENYLOXY(THIO)AL-KYL PHOSPHINATES OR PHOSPHONATES

[75] Inventors: Shy-Fuh Lee, Sunnyvale; Clive A. Henrick, Palo Alto, both of Calif.

[73] Assignee: Zoecon Corporation, Palo Alto, Calif.

[21] Appl. No.: 598,647

[22] Filed: Apr. 10, 1984

Related U.S. Application Data

[60] Division of Ser. No. 433,486, Oct. 8, 1982, Pat. No. 4,456,464, which is a continuation-in-part of Ser. No. 379,587, May 19, 1982, abandoned, which is a continuation-in-part of Ser. No. 317,622, Nov. 2, 1981, abandoned, and a continuation-in-part of Ser. No. 317,623, Nov. 2, 1981, abandoned.

[51] Int. Cl.$^4$ ............................. C07F 9/40; C07F 9/32
[52] U.S. Cl. ..................................................... 260/951

[58] Field of Search ................................ 260/951, 949

[56] References Cited

U.S. PATENT DOCUMENTS 4,182,759  1/1980  Diana ................................... 260/951
4,268,507  5/1981  Mong ................................... 260/951

Primary Examiner—Anton H. Sutto
Attorney, Agent, or Firm—Hana Dolezalova; Jacqueline S. Larson

[57] ABSTRACT

Novel phenoxyphenoxyalkyl-, phenoxyphenylthioalkyl- or phenoxyphenylsulfonylalkyl-substituted phosphinates and phosphonates, related compounds, synthesis thereof, intermediates therefor, and the use of said novel compounds for the control of weeds.

3 Claims, No Drawings

2-NITRO(CYANO)PHENYLOXY(THIO)ALKYL PHOSPHINATES OR PHOSPHONATES

This is a division of application Ser. No. 433,486, filed Oct. 8, 1982, now U.S. Pat. No. 4,456,464, which is a continuation-in-part of Ser. No. 379,587, filed May 19, 1982, now abandoned, which is a continuation-in-part of Ser. No. 317,622, filed on Nov. 2, 1981, now abandoned, and a continuation-in-part of Ser. No. 317,623, filed on Nov. 2, 1981, now abandoned.

The present invention relates to novel phenoxyphenoxyalkyl-, phenoxyphenylthioalkyl- and phenoxyphenylsulfonylalkyl-substituted phosphinates and phosphonates, synthesis thereof, intermediates therefor, and the use of said novel compounds for the control of weeds.

More particularly, the compounds of the present invention are represented by the following formula (A):

(A)

wherein,

R is hydrogen, amino, chloro, cyano or nitro;
n is 0 or 1; n' is 1, 2 or 3;
$R^1$ is hydrogen, lower alkyl, lower haloalkyl, phenyl or benzyl, provided that $R^1$ is not hydrogen when n is 0;
$R^2$ is selected from group (1), (2) or (3)

$$-(CH)_{n'}-\overset{R^4}{\underset{|}{C}}-\overset{W^3}{\underset{\|}{}}-X_n{}^3-R^7, \quad (1)$$

$$-(CH)_{n'}-X^2-\overset{R^4}{\underset{|}{C}}-\overset{W^4}{\underset{\|}{}}-R^3, \text{ or} \quad (2)$$

(3) hydrogen, metal cation, lower alkyl, lower haloalkyl, lower cyanoalkyl, cycloalkyl, cycloalkalkyl, heterocycloalkyl, heterocycloalkalkyl, lower alkenyl, lower haloalkenyl, lower alkynyl, lower haloalkynyl, lower alkoxyalkyl, lower alkylthioalkyl, lower dialkylaminoalkyl, or substituted or unsubstituted aryl;

$R^3$ is lower alkyl, lower haloalkyl, lower alkenyl, lower haloalkenyl, cycloalkyl, cycloalkalkyl, substituted or unsubstituted aryl or $R^3$ and $R^4$ taken together form an alkylene group of 2 to 4 carbon atoms;
each of $R^4$ and $R^6$ is, independently, hydrogen, lower alkyl, lower haloalkyl, lower alkenyl, lower alkynyl, lower alkoxy or lower alkylthio;
$R^7$ is selected from group (3) of $R^2$;
Q is CH or N;
W is oxygen, sulfur, sulfinyl, sulfonyl or $NR^5$ in which $R^5$ is hydrogen or lower alkyl; each of $W^1$, $W^3$ and $W^4$ is, independently, oxygen or sulfur;
$W^2$ is oxygen, sulfur, sulfinyl, sulfonyl, methylene, carbonyl or $NR^5$;
each of X, X' and $X^2$ is, independently, oxygen, sulfur or $NR^5$;
$X^3$ is oxygen, sulfur, methylene or $NR^5$;

each of Y and Z is, independently, hydrogen, lower alkyl, lower haloalkyl, halogen, lower alkoxy, lower haloalkoxy, cyano or nitro; and
t is 1 or 2.

In the description and claims hereinafter, each of n, n', t, Q, $R-R^7$, $W-W^4$, $X-X^3$, Y and Z is as defined above, unless otherwise specified.

The compounds of the present invention of formula (A) can be prepared in accordance with the general processes and examples of synthetic routes described hereinafter.

For example, the following outlined syntheses can be used as generally applicable to preparation of the compounds of formula (A). Herein, $R^{10}$ represents the phenyl or pyridyl ring of formula (A) above.

(I)           (II)

↓

(B)

In the above synthesis, a nitrobenzene (I) is reacted with a phosphinic or phosphonic acid or thioacid (II) at room temperature or above in the presence of a base such as potassium carbonate and a solvent such as 2-butanone, acetone, dimethylformamide or DMSO to give the phosphinate (n=0) or phosphonate (n=1) of formula (B). In formula (II), W is O, S or $NR^5$.

Alternatively, the compounds of formula (A) may be prepared by the reaction of a compound of formula (III) with a haloalkyl phosphinate or phosphonate (IV) or with a mesyloxy phosphinate or phosphonate (VII) under similar conditions as described above. XX is chloro, bromo or iodo. In formula (III), R is $NO_2$, Cl or H and W is O, S or $NR^5$.

(III)        (IV)

(VII)

Compounds of the present invention where $R^2$ is hydrogen (when n=zero) and where $R^1$ and $R^2$ are hydrogen (when n=1), can be prepared, for example, by reaction of a phosphinate or or phosphonate (B) with a strong acid such as hydrochloric acid or with trimethylsilyl bromide in methylene chloride or trichloromethane.

Phosphinate compounds of the present invention where $R^2$ may be other than lower alkyl and where X may be other than oxygen can be prepared from a compound of formula (B) where n=zero by reaction with thionyl chloride or oxalyl chloride at room temperature or above and in a solvent such as ether or methylene chloride and with or without dimethylformamide to give a phosphinic chloride (V). Alternatively, compound (B) (n=zero) may be reacted with phosgene at a temperature below room temperature in a solvent such as benzene or ether. The resulting phosphinic chloride (V) is then reacted with an alcohol, a thiol or an amine corresponding to formula (VI) at room temperature or below in a solvent such as methylene chloride or dimethylformamide and with a base such as triethylamine to give a phosphinate of formula (C).

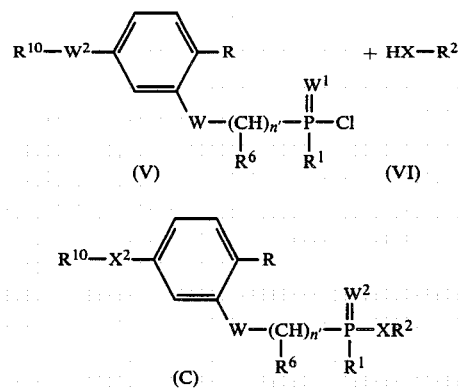

To prepare phosphonate compounds of the present invention where $R^2$ may be other than lower alkyl and where X may be other than oxygen, a compound of formula (B) where n=one is reacted with thionyl chloride at room temperature or above and in a solvent such as benzene or ether to give a phosphonochloridate of formula (Va), which is then reacted with $HXR^2$ (VI) as described above to give a phosphonate of formula (D).

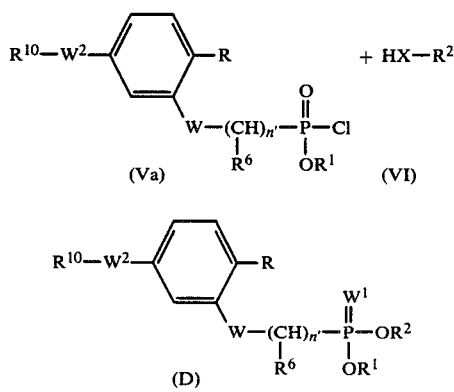

Likewise, to prepare phosphonate compounds of the present invention where each of $R^1$ and $R^2$ may be other than lower alkyl and where each of X and X' may be other than oxygen, a compound of formula (B) (n=one) is reacted neat with thionyl chloride at refluxing temperature to give a phosphonic dichloride of formula (Vb), which is then reacted with $HXR^2$ (VI) as above to give a phosphonate of formula (E).

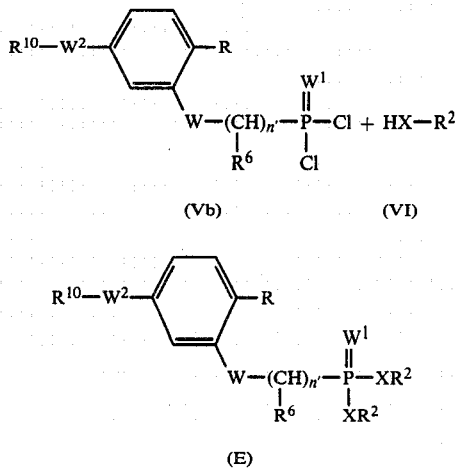

Compounds corresponding to formula (A) where W=sulfonyl are prepared by reacting a compound of formula (A) where W is sulfur with 2 equivalents of m-chloroperbenzoic acid in a solvent such as methylene chloride at room temperature. Compounds where W is sulfinyl are prepared in the same manner, except that 1 equivalent of m-chloroperbenzoic acid is used.

Phosphino- or phosphonothioates of the present invention of formula (A) (where $W^1$ is sulfur) can be prepared by reaction of a phosphinate or phosphonate (A where $W^1$ is oxygen) with, for example, phosphorus pentasulfide at an elevated temperature.

The compounds of formula (A) where R=cyano or chloro can be produced by the hydrogenation of a phosphinate (A) where R=nitro to an amino compound (A where R=amino), which is diazotized following the procedure described in Org. Synth. Coll. Vol. 1:514 (1932). The diazo salt is then reacted with cuprous cyanide or cuprous chloride to give the corresponding cyano compound (A where R=cyano) or chloro compound (A where R=chloro).

Compounds of formula (A) where R=alkylcarbonylamino or alkylsulfonylamino can be prepared by the reaction on an amino compound (A where R=amino) with a carbonyl halide

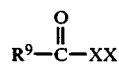

or a sulfonyl halide $R^9$—$SO_2$—XX ($R^9$=lower haloalkyl; XX=Cl or Br) in the presence of, for example, triethylamine or potassium carbonate and a solvent such as acetone or methylene chloride, the reaction most usually taking place at room temperature.

Compounds of formula (A) wherein $R^2$ represents the values of group (2) can be prepared from an acid or salt thereof of formula (I') and a compound of formula (II') to form a compound of formula (F).

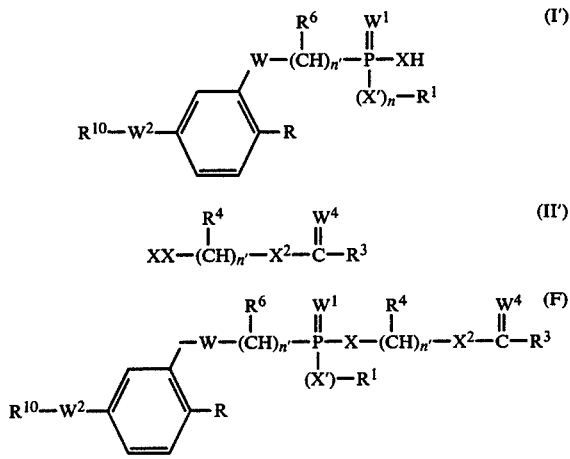

Compounds of formula (II') can be prepared by the methods described by Ulich and Adams, *J.A.C.S.* 43, 660 (1921).

Compounds of formula (A) wherein $R^2$ represents the values of group (1) can be prepared from an acid or salt thereof of formula (I') and a compound of formula (II'A).

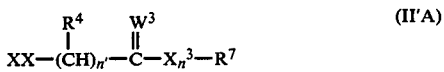

Alternatively, the compounds of formula (F) can be prepared by reaction of an acid chloride of formula (V) with an alcohol, thiol or amine of formula (II") in which n' is 2 or 3.

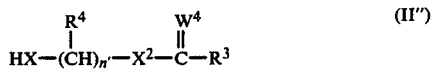

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms. The term "lower cyanoalkyl" refers to a lower alkyl group substituted with a cyano moiety.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower alkoxyalkyl" refers to a lower alkyl group substituted with a lower alkoxy group.

The term "lower alkylthioalkyl" refers to a lower alkyl group substituted with a lower alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds. The term "lower haloalkenyl" refers to a lower alkenyl group substituted with one to three halogen atoms.

The term "lower alkynyl" refers to an alkynyl group, straight or branched, having a chain length of two to eight carbon atoms and one to two acetylenic bonds.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve.

The term "heterocycloalkyl" refers to a cycloalkyl group of three to eight cyclic carbon atoms wherein one ring carbon atom is replaced by an oxygen atom or a nitrogen atom. The term "heterocycloalkalkyl" refers to a heterocycloalkyl group as defined herein wherein one hydrogen atom is replaced by a lower alkyl group of one to four carbon atoms.

The term "dialkylaminoalkyl" refers to an aminoalkyl group, straight or branched, of one to eight carbon atoms wherein each of the two hydrogen atoms attached to the nitrogen atom is replaced by a lower alkyl group, as defined herein.

The term "lower alkylsulfonyl" refers to an alkylsulfonyl group, straight or branched, of one to eight carbon atoms. The term "haloalkylsulfonyl" refers to a lower alkylsulfonyl group substituted with one to three halogen atoms.

The term "aryl" refers to a phenyl, benzyl or phenethyl group. "Substituted aryl" refers to an aryl group substituted at one, two or three of the ring carbon atoms with a group selected from lower alkyl, lower haloalkyl, lower alkoxy, lower haloalkoxy, halogen, nitro, or cyano.

The term "metal cation" refers to a metal cation conventionally used in making herbicidally active salts such as sodium, potassium, calcium, ammonium, and the like.

The compounds of formula (A) are useful for the control of weeds, using pre- and/or post-emergent treatments (foliar, soil and/or floodwater applications). The compounds can be applied in the form of dusts, granules, solutions, emulsions, wettable powders, flowables and suspensions. Application of a compound of the present invention is made according to conventional procedure to the weeds or their locus using a herbicidally effective amount of the compound, usually from about one-half or less to ten pounds per acre.

Methods of preparing herbicidal formulation which can be used with a compound of the present invention are described in the literature along with suitable liquid and solid carriers such as in U.S. Pat. Nos. 4,192,669 and 4,163,661 which are incorporated herein by reference. The compounds of the present invention have herbicidal activity on both broad leaf plants such as pigweed, annual morning glory, sicklepod, mustard, velvetleaf, sesbania sp., and curlydock; and the grassy weeds such as green foxtail, barnyard grass, wild oat and shattercane; and such weeds as yellow nutsedge. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

The compounds of formula (A) are useful pesticides for the control of insects of the, for example, order Diptera such as flies and mosquitoes.

The following examples are provided to illustrate the practice of the present invention. Temperature is given in degrees Centigrade. "RT" means room temperature.

EXAMPLE 1

A mixture of 4-(2-chloro-4-trifluoromethylphenoxy)-1,2-dinitrobenzene (500 mg, 1.38 mmol), diethyl hydroxymethylphosphonate (295 mg, 1.66 mmol) and potassium carbonate (285 mg, 2.07 mmol) in 2-butanone (5 ml) is heated under reflux for 6 hours. After cooling, the reaction mixture is filtered, and the filtrate is concentrated to dryness. The crude product is purified by preparative thin layer chromatography (prep. TLC) (silica gel, developed with 50% ethyl acetate/hexane) to give diethyl 2-nitro-5-(2-chloro-4-trifluoromethylphenoxy)phenoxymethyl-phosphonate.

EXAMPLE 2

Following the procedure of Example 1, dimethyl 2-nitro-5-(2-chloro-4-trifluoromethylphenoxy)phenoxymethylphosphonate is prepared from 4-(2-chloro-4-trifluoromethylphenoxy)-1,2-dinitrobenzene and dimethyl hydroxymethylphosphonate.

nmr (CDCl$_3$) δ 5.69 (d, 2H, OCH$_2$—P and 6.12 ppm (d, 6H, 10 Hz, OCH$_3$).

In the same way, 4-(2-chloro-4-trifluoromethylphenoxy)-1,2-dinitrobenzene is reacted with each of dimethyl hydroxyethylphosphonate and dimethyl hydroxy-n-propylphosphonate to yield, respectively, dimethyl 2-nitro-5-(2-chloro-4-trifluoromethylphenoxy)-phenoxyethylphosphonate (A; m' is 2, R$^6$ is H) and dimethyl 2-nitro-5-(2-chloro-4-trifluoromethylphenoxy)phenoxy-n-propylphosphonate (A; n' is 3, R$^6$ is H).

EXAMPLE 3

Following the procedure of Example 1, dimethyl hydroxymethylphosphonate is reacted with each of the dinitrobenzenes in Column I to give the corresponding phosphonate in Column II.

I 4-(2,6-dichloro-4-trifluoromethylphenoxy)-1,2-dinitrobenzene
4-(4-chloro-2-nitrophenoxy)-1,2-dinitrobenzene
4-(2-cyano-4-trifluoromethylphenoxy)-1,2-dinitrobenzene
4-(2-nitro-4-trifluoromethylphenoxy)-1,2-dinitrobenzene
4-(4-chlorophenoxy)-1,2-dinitrobenzene
4-(4-trifluoromethylphenoxy)-1,2-dinitrobenzene
4-(2-bromo-4-chlorophenoxy)-1,2-dinitrobenzene
4-(2,4-dichlorophenoxy)-1,2-dinitrobenzene

II dimethyl 2-nitro-5-(2,6-dichloro-4-trifluoromethylphenoxy)phenoxymethylphosphonate
dimethyl 2-nitro-5-(4-chloro-2-nitrophenoxy)phenoxymethylphosphonate
dimethyl 2-nitro-5-(2-cyano-4-trifluoromethylphenoxy)phenoxymethylphosphonate
dimethyl 2-nitro-5-(2-nitro-4-trifluoromethylphenoxy)phenoxymethylphosphonate
dimethyl 2-nitro-5-(4-chlorophenoxy)phenoxymethylphosphonate
dimethyl 2-nitro-5-(4-trifluoromethylphenoxy)phenoxymethylphosphonate
dimethyl 2-nitro-5-(2-bromo-4-chlorophenoxy)phenoxymethylphosphonate
dimethyl 2-nitro-5-(2,4-dichlorophenoxy)phenoxymethylphosphonate

EXAMPLE 4

To dimethyl 2-nitro-5-(2-chloro-4-trifluoromethylphenoxy)phenoxymethylphosphonate (0.5 g) in benzene (10 ml) is added thionyl chloride (8 ml) at RT. The mixture is allowed to return to RT and is stirred for 6 hours. The solvent and any excess thionyl chloride are then distilled off, yielding methyl 2-nitro-5-(2-chloro-4-trifluoromethylphenoxy)phenoxymethylphosphonochloridate.

To a solution of methyl 2-nitro-5-(2-chloro-4-trifluoromethylphenoxy)phenoxymethylphosphonochloridate (20 mmol) in methylene chloride (30 ml) is added 2-propenol (30 mmol) and triethylamine (20 mmol). The mixture is stirred at RT for about 2 hours. The reaction mixture is then washed with water, and the organic layer is dried and evaporated to dryness to give methyl 2-propenyl 2-nitro-5-(2-chloro-4-trifluoromethylphenoxy)phenoxymethylphosphonate.

In the same way, methyl 2-nitro-5-(2-chloro-4-trifluoromethylphenoxy)phenoxymethylphosphonic chloride is reacted with each of the compounds in column III to prepare the corresponding phosphonate, phosphonothioate or phosphonamide in Table IV of formula (IV') wherein Y is Cl, Z is CF$_3$, R is NO$_2$, R$^1$ is CH$_3$ and W$^2$ is O.

III 2-propynol
3,3-dichloro-2-propenol
hydroxyacetonitrile
benzyl alcohol
ethyl hydroxyacetate
2-methoxyethanol
4-chlorophenol
2-tetrahydrofuryl methanol
cyclohexylmethanol
methyl thiol
benzyl thiol
ethyl sulfhydrylacetate
isopropylamine
methylsulfonamide
ethyl aminoacetate

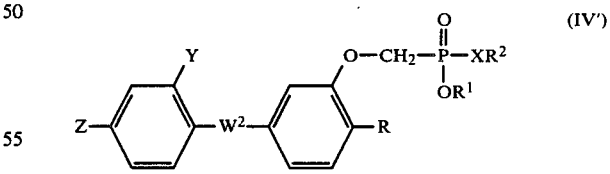

(IV')

TABLE IV

| XR$^2$ |
| --- |
| —O—CH$_2$—C≡CH |
| —O—CH$_2$—CH=C(Cl)(Cl) |
| —O—CH$_2$CN |

TABLE IV-continued

XR²

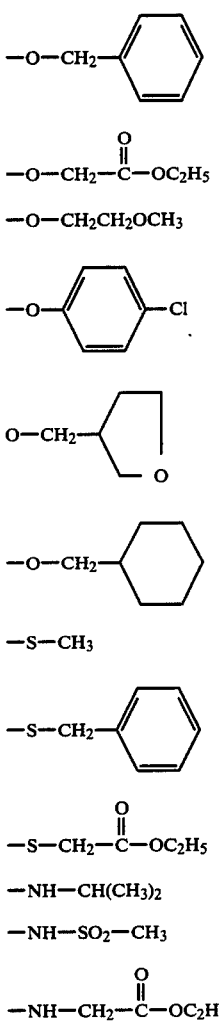

EXAMPLE 5

A mixture of dimethyl 2-nitro-5-(2-chloro-4-trifluoromethylphenoxy)phenoxymethylphosphonate (1.5 g) and thionyl chloride (10 ml) is heated under reflux for 2 hours. Any excess thionyl chloride is then removed to yield 2-nitro-5-(2-chloro-4-trifluoromethylphenoxy)-phenoxymethylphosphonic dichloride.

To a solution of 2-nitro-5-(2-chloro-4-trifluoromethylphenoxy)phenoxymethylphosphonic dichloride (20 mmol) in methylene chloride (30 ml) is added allyl alcohol (50 mmol) and triethylamine (20 mmol). The mixture is stirred at RT for about 1 hour. It is then washed with water and the organic layer is dried and evaporated to dryness to give di(2-propenyl)2-nitro-5-(2-chloro-4-trifluoromethylphenoxy)phenoxymethylphosphonate.

In the same way, each of the compounds in Column V is reacted with 2-nitro-5-(2-chloro-4-trifluoromethylphenoxy)phenoxymethylphosphonic dichloride to prepare the corresponding phosphonate in Column VI.

V phenol
hydroxyacetonitrile
methylthiol
isopropylamine

VI diphenyl 2-nitro-5-(2-chloro-4-trifluoromethylphenoxy)phenoxymethylphosphonate
di(cyanomethyl)2-nitro-5-(2-chloro-4-trifluoromethylphenoxy)phenoxymethylphosphonate
dimethyl 2-nitro-5-(2-chloro-4-trifluoromethylphenoxy)phenoxymethylphosphonodithioate
diisopropyl 2-nitro-5-(2-chloro-4-trifluoromethylphenoxy)phenoxymethylphosphonamide

EXAMPLE 6

2-nitro-5-(2-chloro-4-trifluoromethylphenoxy)-phenoxymethylphosphonic dichloride (22 mmol) is dissolved in methylene chloride (30 ml), and through this solution is passed dimethylamine at 0° for 2 minutes. The reaction mixture is then washed with water, dried and evaporated to give N,N,N',N'-tetramethyl 2-nitro-5-(2-chloro-4-trifluoromethylphenoxy)phenoxymethylphosphonamide.

In the same way, methyl N,N-dimethyl 2-nitro-5-(2-chloro-4-trifluoromethylphenoxy)phenoxymethylphosphonamide is prepared from methyl 2-nitro-5-(2-chloro-4-trifluoromethylphenoxy)phenoxymethylphosphonic chloride and dimethylamine.

EXAMPLE 7

A mixture of 4-(2-chloro-4-trifluoromethylphenoxy)-1,2-dinitrobenzene (569 mg, 1.57 mmol), potassium carbonate (303 mg, 2.36 mmol), diethyl sulfhydrylmethylphosphonate (405 mg, 2.20 mmol) and 2-butanone (5 ml) is heated under reflux for 5 hours. The reaction mixture is then filtered, and the filtrate is concentrated to dryness and purified by prep. TLC to give diethyl 2-nitro-5-(2-chloro-4-trifluoromethylphenoxy)phenylthiomethylphosphonate. NMR (CDCl₃) δ 5.87 (m, 4H, OC$\underline{H}_2$CH₃), 6.90 (d, 2H, 14 Hz, SCH₂—P) and 8.63 ppm (t, 6H, OCH₂C$\underline{H}_3$).

In like manner, 4-(2-chloro-4-trifluoromethylphenoxy)-1,2-dinitrobenzene and dimethyl sulfhydrylmethylphosphonate is reacted together to yield dimethyl 2-nitro-5-(2-chloro-4-trifluoromethylphenoxy)phenylthiomethylphosphonate.

Following the same procedure, dimethyl sulfhydrylmethylphosphonate is reacted with each of 4-(2,6-dichloro-4-trifluoromethylphenoxy)-1,2-dinitrobenzene, 4-(4-chloro-2-nitrophenoxy)-1,2-dinitrobenzene, 4-(2,4-dichlorophenoxy)-1,2-dinitrobenzene and 4-(4-trifluoromethylphenoxy)-1,2-dinitrobenzene to yield, respectively, dimethyl 2-nitro-5-(2,6-dichloro-4-trifluoromethylphenoxy)phenylthiomethylphosphonate,
dimethyl 2-nitro-5-(4-chloro-2-nitrophenoxy)phenylthiomethylphosphonate,
dimethyl 2-nitro-5-(2,4-dichlorophenoxy)phenylthiomethylphosphonate, and
dimethyl 2-nitro-5-(4-trifluoromethylphenoxy)phenylthiomethylphosphonate.

EXAMPLE 8

Following the procedure of Example 1, 4-(2-chloro-4-trifluoromethylphenoxy)-1,2-dinitrobenzene is reacted with each of the phosphinates listed in Column VII to yield the corresponding phosphinate in Table VIII of formula (VIII') wherein R is NO₂, W¹ is O, X is O, R⁶ is H, W² is O, Y is Cl, Z is CF₃ and Y' is H.

VII ethyl methylhydroxymethylphosphinate
ethyl ethylhydroxymethylphosphinate
methyl ethylhydroxymethylphosphinate
methyl methylhydroxymethylphosphinate
methyl methylhydroxyethylphosphinate
methyl methylhydroxy-n-propylphosphinate
methyl methylsulfhydrylmethylphosphinate
ethyl ethylsulfhydrylmethylphosphinate

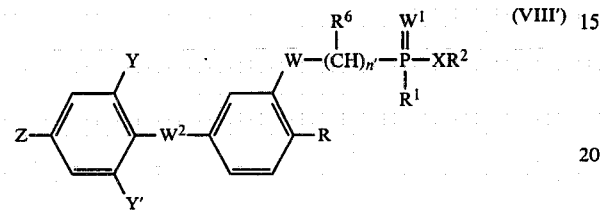

(VIII')

TABLE VIII

| R¹    | R²    | W | n' |
|-------|-------|---|----|
| CH₃   | C₂H₅  | O | 1  |
| C₂H₅  | C₂H₅  | O | 1  |
| C₂H₅  | CH₃   | O | 1  |
| CH₃   | CH₃   | O | 1  |
| CH₃   | CH₃   | O | 2  |
| CH₃   | CH₃   | O | 3  |
| CH₃   | CH₃   | S | 1  |
| C₂H₅  | C₂H₅  | S | 1  |

EXAMPLE 9

Following the procedure of Example 1, methyl methylhydroxymethylphosphinate is reacted with each of the dinitrobenzenes listed in Column I (Example 3) to give the corresponding phosphinate in Table IX of formula (VIII') wherein R is NO₂, R¹ is CH₃, R² is CH₃ R⁶ is H, n' is 1, W=W¹=W²=X is O.

TABLE IX

| Y    | Z    | Y' |
|------|------|-----|
| Cl   | CF₃  | Cl  |
| NO₂  | Cl   | H   |
| CN   | CF₃  | H   |
| NO₂  | CF₃  | H   |
| H    | Cl   | H   |
| H    | CF₃  | H   |
| Br   | Cl   | H   |
| Cl   | Cl   | H   |

EXAMPLE 10

Following the procedure of Example 4, methyl P-methyl-2-nitro-5-(2-chloro-4-trifluoromethylphenoxy)-phenoxymethylphosphinate is reacted with thionyl chloride to give P-methyl-2-nitro-5-(2-chloro-4-trifluoromethylphenoxy)phenoxymethylphosphinic chloride.

P-methyl-2-nitro-5-(2-chloro-4-trifluoromethylphenoxy)phenoxymethylphosphinic chloride is then reacted with allyl alcohol and with each of the compounds listed in Column III (Example 4) to give the corresponding phosphinate, phosphinothioate or phosphinamide in Table X of formula (VIII') wherein R is NO₂, R¹ is CH₃, R⁶ is H, n' is 1, Y' is H, Y is Cl, Z is CF₃ and W=W¹=W² is O.

TABLE X

—XR²

OCH₂—CH=CH₂
OCH₂—C≡CH
OCH₂—CH=CCl₂
OCH₂—CN

OCH₂—⟨phenyl⟩

OCH₂—C(=O)—OC₂H₅

OCH₂CH₂OCH₃

O—⟨C₆H₄⟩—Cl

O—CH₂—⟨tetrahydrofuran⟩

O—CH₂—⟨cyclohexyl⟩

SCH₃

S—CH₂—⟨phenyl⟩

S—CH₂—C(=O)—OC₂H₅
NH—CH(CH₃)₂
NH—SO₂—CH₃

NH—CH₂—C(=O)—OC₂H₅

Further, P-methyl-2-nitro-5-(2-chloro-4-trifluoromethylphenoxy)phenoxymethylphosphinic chloride may be reacted with dimethylamine, following the procedure of Example 6, to yield N,N-dimethyl P-methyl-2-nitro-5-(2-chloro-4-trifluoromethylphenoxy)phenoxymethylphosphinamide.

EXAMPLE 11

A mixture of dimethyl 2-nitro-5-(2-chloro-4-trifluoromethylphenoxy)phenylthiomethylphosphonate (25 mmol) and m-chloroperbenzoic acid (50 mmol) in methylene chloride (20 ml) is stirred at RT for 1 hour. Calcium chloride (4×weight) is then added to the reaction mixture. The mixture is stirred for 10 minutes and is then filtered. Solvent is removed and the product is dried and evaporated to dryness to give dimethyl 2-nitro-5-(2-chloro-4-trifluoromethylphenoxy)phenylsulfonylmethylphosphonate.

In the same way, methyl P-methyl-2-nitro-5-(2-chloro-4-trifluoromethylphenoxy)phenylsulfonylmethylphosphinate is prepared by the reaction of methyl P-methyl-2-nitro-5-(2-chloro-4-trifluoromethylphenoxy)phenylthiomethylphosphinate and m-chloroperbenzoic acid.

EXAMPLE 12

A solution of methyl P-methyl-2-nitro-5-(2-chloro-4-trifluoromethylphenoxy)phenoxymethylphosphinate (5.5 mmol) in methanol (10 ml) is hydrogenated with 10% Pd/C (200 mg) at 1 atmosphere for 30 min. to give, after filtration and removal of the solvent, methyl P-methyl-2-amino-5-(2-chloro-4-trifluoromethylphenoxy)phenoxymethylphosphinate.

In the same way, dimethyl 2-nitro-5-(2-chloro-4-trifluoromethylphenoxy)phenoxymethylphosphonate is hydrolyzed to yield dimethyl 2-amino-5-(2-chloro-4-trifluoromethylphenoxy)phenoxymethylphosphonate.

EXAMPLE 13

Following the procedure described in *Org. Synth. Coll. Vol.* 1, p. 514 (1932), each of methyl P-methyl-2-amino-5-(2-chloro-4-trifluoromethylphenoxy)phenoxymethylphosphinate and dimethyl 2-amino-5-(2-chloro-4-trifluoromethylphenoxy)phenoxymethylphosphonate is diazotized. Each of the resulting diazo salts is treated with cuprous cyanide (1.2 eq.) in benzene/water solution. When the reaction is completed, the organic phase is separated, washed with water, dried and purified by prep. TLC to yield, respectively, methyl P-methyl-2-cyano-5-(2-chloro-4-trifluoromethylphenoxy)phenoxymethylphosphinate, and dimethyl 2-cyano-5-(2-chloro-4-trifluoromethylphenoxy)phenoxymethylphosphonate.

In the same way, each of the above two diazo salts is treated with cuprous chloride to give, respectively, methyl P-methyl-2-chloro-5-(2-chloro-4-trifluoromethylphenoxy)phenoxymethylphosphinate, and dimethyl 2-chloro-5-(2-chloro-4-trifluoromethylphenoxy)phenoxymethylphosphonate.

EXAMPLE 14

To a mixture of methyl P-methyl-2-amino-5-(2-chloro-4-trifluoromethylphenoxy)phenoxymethylphosphinate (2.5 mmol) and potassium carbonate (0.4 ml) in acetone (20 ml) is added chloroacetyl chloride (3.8 mmol). The mixture is stirred at RT for about 2 hours, after which it is washed with water, dried, evaporated and purified by prep. TLC to yield methyl P-methyl-2-chloroacetamido-5-(2-chloro-4-trifluoromethylphenoxy)phenoxymethylphosphinate.

In the same way, dimethyl 2-chloroacetamido-5-(2-chloro-4-trifluoromethylphenoxy)phenoxymethylphosphonate is prepared from dimethyl 2-amino-5-(2-chloro-4-trifluoromethylphenoxy)phenoxymethylphosphonate and chloroacetyl chloride.

EXAMPLE 15

Dimethyl 2-nitro-5-(2-chloro-4-trifluoromethylphenoxy)phenoxymethylphosphonate (1 g) in 20 ml of 6N hydrochloric acid is heated under reflux overnight. The solution is then poured into water and the mixture is extracted with methylene chloride. The combined solvent extracts are dried over magnesium sulfate and the solvent is then evaporated off to give 2-nitro-5-(2-chloro-4-trifluoromethylphenoxy)phenoxymethylphosphonic acid.

In the same way, each of methyl P-methyl-2-nitro-5-(2-chloro-4-trifluoromethylphenoxy)phenoxymethylphosphinate and ethyl P-ethyl-2-nitro-5-(2-chloro-4-trifluoromethylphenoxy)phenoxymethylphosphinate is treated with 6N HCl to yield, respectively, P-methyl-2-nitro-5-(2-chloro-4-trifluoromethylphenoxy)phenoxymethylphosphinic acid and P-ethyl-2-nitro-5-(2-chloro-4-trifluoromethylphenoxy)phenoxymethylphosphinic acid.

EXAMPLE 16

A mixture of 5-(2-chloro-4-trifluoromethylphenoxy)-2-nitrophenol (2.5 mmol), chloromethyl methylphosphinic acid (3.8 mmol), potassium carbonate (5.0 mmol) and dimethylformamide (5 ml) is heated to 120° for 2 hours. The reaction mixture is then acidified and extracted with ether. The combined ether extracts are washed with water, dried and evaporated to dryness to yield P-methyl-2-nitro-5-(2-chloro-4-trifluoromethylphenoxy)phenoxymethylphosphinic acid.

In the same way, P-methyl-2-nitro-5-(2-chloro-4-trifluoromethylphenoxy)phenylthiomethylphosphinic acid is prepared from 5-(2-chloro-4-trifluoromethylphenoxy)-2-nitrophenyl thiol and chloromethyl methylphosphinic acid.

EXAMPLE 17

A mixture of ethyl P-ethyl-2-nitro-5-(2-chloro-4-trifluoromethylphenoxy)phenoxymethylphosphinate (4.7 mmol) and phosphorus pentasulfide (1.2 mmol) is heated to 150°–160° under nitrogen for 3–4 hours. After cooling, the residue is purified by prep. TLC to give O-ethyl P-ethyl-2-nitro-5-(2-chloro-4-trifluoromethylphenoxy)phenoxymethylphosphinothioate.

In the same way, dimethyl 2-nitro-5-(2-chloro-4-trifluoromethylphenoxy)phenoxymethylphosphonate and phosphorus pentasulfide are reacted together to yield O,O'-dimethyl 2-nitro-5-(2-chloro-4-trifluoromethylphenoxy)phenoxymethylphosphonothioate.

EXAMPLE 18

Post-emergence herbicidal activity on the grasses green foxtail, watergrass, shattercane and wild oats and on the broadleafs annual morning glory, mustard, soybean and velvetleaf was tested for the compound of Example 1 by spraying seedlings with a solution of water/acetone (1:1), surfactant (1%) and test compound at a rate equivalent to 10 lb/acre. The average herbicidal activity, in percent control, is 99% in the grasses and 95% in the broadleafs.

Pre-emergence herbicidal activity of the compound of Example 1 was tested on the above grasses and broadleafs (except that nightshade was substituted for soybean) at a rate equivalent to 10 lb/acre. The average activity, in percent control, is 81% in the grasses and 95% in the broadleafs.

EXAMPLE 19

To a mixture of ethyl P-methylphosphite (20 g, 185.0 mmol) and acetaldehyde (12 ml) is added, dropwise, saturated sodium ethoxide until the inside temperature is raised to the maximum. The reaction mixture is then filtered to give ethyl P-methyl α-hydroxyethylphosphinate.

To a solution of the above phosphinate (10 g, 65.0 mmol) in methylene chloride (20 ml) containing triethylamine (10.9 ml) is added, dropwise at 0°, methanesulfonyl chloride (7.6 ml, 104.0 mmol). After addition is complete, the mixture is stirred at RT for 4 hours. It is then diluted with methylene chloride, washed with brine, dried and concentrated to dryness. The crude product is purified by prep. TLC (silica gel, developing with 10% ethanol/chloroform) to give ethyl P-methyl α-mesyloxyethylphosphinate.

A mixture of 5-(2-chloro-4-trifluoro-methylphenoxy)-2-nitrophenol (1.1 g, 3.3 mmol), ethyl P-methyl α-mesyloxyethylphosphinate (1.2 g, 5.3 mmol), potassium carbonate (0.68 g, 1.5 eq.) and 2-butanone (20 ml) is heated under reflux for 2 days and is then filtered. The filtrate is concentrated to dryness to give an oily residue. The residue is taken up in methylene chloride, washed, dried and evaporated to dryness. The resulting crude product is purified by prep. TLC (silica gel, developing with 50% ethyl acetate/hexane) to give ethyl P-methyl-α-[2-nitro-5-(2-chloro-4-trifluoromethylphenoxy)phenoxy]ethylphosphinate (VIII'; R is $NO_2$, $R^1=R^6$ is $CH_3$, n' is 1, $R^2$ is $C_2H_5$, $W=W^1=W^2=X$ is O, Y' is H, Y is Cl, Z is $CF_3$).

nmr ($CDCl_3$) δ 8.35 (d, 3H, 14.5 Hz, P—$CH_3$), 8.62 (t, 3H, $OCH_2CH_3$), 8.60 (q, 3H, $OCH(CH_3)P$), 5.87 (quintet, 2H, $OCH_2CH_3$), 5.42 (quintet, 1H, $OCH(CH_3)P$).

EXAMPLE 20

To ethyl P-methyl-α-[2-nitro-5-(2-chloro-4-trifluoromethylphenoxy)phenoxy]ethylphosphinate (1.1 g) in ethanol (10 ml) is added potassium hydroxide (0.5 g) in water (15 ml). The mixture is stirred at RT for 4 hours. The ethanol is removed, and the aqueous solution is acidified and extracted with ether. The combined extracts are dried and evaporated to dryness to give P-methyl-α-[2-nitro-5-(2-chloro-4-trifluoromethylphenoxy)phenoxy]-ethylphosphinic acid.

nmr ($CDCl_3$) δ 8.47 (q, 3H, $OCH(CH_3)P$), 8.42 (d, 3H, 14.5 HZ, P—$CH_3$), 5.44 (m, 1H, $OCH(CH_3)P$).

EXAMPLE 21

The phosphinic acid of Example 20 is reacted with an excess of diazomethane in ether to give methyl P-methyl-α-[2-nitro-5-(2-chloro-4-trifluoromethylphenoxy)-phenoxy]ethylphosphinate.

nmr ($CDCl_3$) δ 8.57, 8.43 (qq, 3H, $OCH(CH_3)P$), 8.35 (d, 3H, 14.5 Hz, P—$CH_3$), 6.27, 6.17 (dd, 3H, $POCH_3$), 5.30 (m, 1H, $OCH(CH_3)P$).

EXAMPLE 22

A mixture of the phosphinic acid of Example 20 (0.50 g, 1.1 mmol), methyl bromoacetate (0.2 ml, 2.2 mmol), potassium carbonate (0.24 g, 1.6 mmol) and 2-butanone (20 ml) is heated under reflux overnight. It is then filtered and the filtrate is concentrated to dryness. The crude product is purified by prep. TLC (60% ethyl acetate/hexane) to give methoxycarbonylmethyl P-methyl-α-[2-nitro-5-(2-chloro-4-trifluoromethylphenoxy)ethylphosphinate.

nmr ($CDCl_3$) δ 8.42 (q, 3H, $OCH(CH_3)P$), 8.25 (d, 3H, 14.5 Hz, P—$CH_3$), 6.30, 6.25 (ss, 3H, $OCH_3$), 5.47, 5.40 (dd, 2H, 12.5 Hz, $OCH_2C(O)$).

In the same way, P-methyl-α-[2-nitro-5-(2-chloro-4-trifluoromethylphenoxy)phenoxy]ethylphosphinic acid and ethyl bromoacetate are reacted together to give ethoxycarbonylmethyl P-methyl-α-[2-nitro-5-(2-chloro-4-trifluoromethylphenoxy)phenoxy]ethylphosphinate.

EXAMPLE 23

Following the procedure of Example 19, ethyl P-methyl-α-mesyloxyethylphosphinate is reacted with each of 5-(2-fluoro-4-trifluoromethylphenoxy)-2-nitrophenol, 5-(2-methyl-4-trifluoromethylphenoxy)-2-nitrophenol, 5-(4-chloro-2-nitrophenoxy)-2-nitrophenol and 5-(2,6-dichloro-4-trifluoromethylphenoxy)-2-nitrophenol to yield, respectively, ethyl P-methyl-α-[2-nitro-5-(2-fluoro-4-trifluoromethylphenoxy)phenoxy]ethylphosphinate,
ethyl P-methyl-α-[2-nitro-5-(2-methyl-4-trifluoromethylphenoxy)phenoxy]ethylphosphinate,
ethyl P-methyl-α-[2-nitro-5-(4-chloro-2-nitrophenoxy)phenoxy]ethylphosphinate, and
ethyl P-methyl-α-[2-nitro-5-(2,6-dichloro-4-trifluoro methylphenoxy)phenoxy]ethylphosphinate.

EXAMPLE 24

A mixture of 4-(2-chloro-4-trifluoromethylphenoxy)-1,2-dinitrobenzene (600 mg), dimethyl α-hydroxyethylphosphonate (382 mg), potassium carbonate (343 mg) and 2-butanone (8 ml) is heated under reflux for 24 hours. The reaction mixture is filtered, and the filtrate is concentrated and purified by prep. TLC to give dimethyl α-[2-nitro-5-(2-chloro-4-trifluoromethylphenoxy)phenoxy]ethylphosphonate.

nmr ($CDCl_3$) δ 8.40 (dd, 3H, $OCH(CH_3)P$), 6.17 (d, 6H, 10.5 Hz, $P(OCH_3)_2$), 5.30 (m, 1H, $OCH(CH_3)P$).

In the same way, diethyl α-hydroxyethylphosphonate and 4-(2-chloro-4-trifluoromethylphenoxy)-1,2-dinitrobenzene are reacted together to yield diethyl α-[2-nitro-5-(2-chloro-4-trifluoromethylphenoxy)phenoxy]ethylphosphonate (VIII'; R is $NO_2$, $R^1$ is $OC_2H_5$, $R^2$ is $C_2H_5$, $R^6$ is $CH_3$, n' is 1, $W=W^1=W^2=X$ is O, Y' is H, Y is Cl, Z is $CF_3$).

EXAMPLE 25

A mixture of ethyl P-methyl mesyloxymethylphosphinate (540 mg, 2.5 mmol), 5-(2-chloro-4-trifluoromethylphenoxy)-2-nitrophenol (589 mg, 1.8 mmol), potassium carbonate (366 mg, 1.5 eq.) and 2-butanone (10 ml) is heated under reflux for 20 hours. The reaction mixture is filtered, and the filtrate is concentrated. The oily crude product is taken up in methylene chloride, washed, dried and concentrated to dryness to give ethyl P-methyl-2-nitro-5-(2-chloro-4-trifluoromethylphenoxy)phenoxymethylphosphinate.

nmr ($CDCl_3$) δ8.67 (t, 3H, $OCH_2CH_3$), 8.30 (d, 3H, 14.5 Hz, P—$CH_3$), 5.87 (q, 2H, $OCH_2CH_3$), 5.74 (d, 2H, 8 Hz, $OCH_2P$), [3.50 (dd, 1H, 8 Hz), 3.27 (d, 1H, 2 Hz), 2.80 (d, 1H, 8 Hz), 2.37 (dd, 1H, 8 Hz), 2.24 (d, 1H, 2 Hz), 2.07 (d, 1H, 8 Hz) two aromatic H].

Ethyl P-methyl mesyloxymethylphosphinate is prepared from ethyl P-methyl hydroxymethylphosphinate and methanesulfonyl chloride, following the procedure of Example 19.

EXAMPLE 26

To ethyl P-methyl-2-nitro-5-(2-chloro-4-trifluoromethylphenoxy)phenoxymethylphosphinate (1.30 g) in ethanol (10 ml) is added 5% aq. sodium hydroxide (20 ml) and the solution is stirred at RT for 20 minutes. The ethanol is evaporated off; the aqueous solution is extracted with ether and the ether layer is discarded. The basic aqueous solution is acidified with dilute HCl and extracted with methylene chloride. The combined organic extracts are washed, dried and evaporated to dryness to give P-methyl-2-nitro-5-(2-chloro-4-trifluoromethylphenoxy)phenoxymethylphosphinic acid (IX; R is $NO_2$, $R^1$ is $CH_3$, $R^2=R^6$ is H, W=X is O, Y is Cl, Z is $CF_3$).

nmr ($CDCl_3$) δ8.30 (d, 3H, 14.5 Hz, P—$CH_3$), 5.74 (d, 2H, 8 Hz, $OCH_2P$), [3.50 (dd, 1H, 8 Hz), 3.27 (d, 1H, 2 Hz), 2.80 (d, 1H, 8 Hz), 2.37 (dd, 1H, 8 Hz), 2.24 (d, 1H, 2 Hz), 2.07 (d, 1H, 8 Hz) two aromatic H].

EXAMPLE 27

Following the procedure of Example 22, the phosphinic acid of Example 26 (400 mg, 0.94 mmol) and methyl bromoacetate (287 mg, 8.8 mmol) are reacted together with potassium carbonate (194 mg, 1.5 eq.) and 2-butanone (10 ml), to yield methoxycarbonylmethyl P-methyl-2-nitro-5-(2-chloro-4-trifluoromethylphenoxy)phenoxymethylphosphinate.

nmr ($CDCl_3$) δ8.20 (d, 3H, 14.5 Hz, P—$CH_3$), 6.42 (s, 3H, $OCH_3$), 5.60 (d, 2H, 8 Hz, $OCH_2P$), 5.37 (d, 2H, 12.5 Hz, $OCH_2C(O)$).

EXAMPLE 28

To a solution of the phosphinic acid of Example 26 (400 mg) in methylene chloride (5 ml) is added, dropwise, diazomethane until a yellow solution is obtained. Excess diazomethane is removed, and the solution is evaporated to dryness to yield methyl P-methyl-2-nitro-5-(2-chloro-4-trifluoromethylphenoxy)phenoxy)methylphosphinate.

nmr ($CDCl_3$) δ8.32 (d, 3H, 14.5 Hz, P—$CH_3$) 6.24 (d, 3H, 10.5 Hz, P—$OCH_3$), 5.74 (d, 2H, 8 Hz, $OCH_2P$).

EXAMPLE 29

Following the procedure of Example 18, each of the final compounds of Examples 25, 26, 27 and 28 (compounds 2, 3, 4 and 5, respectively), is tested for post-emergence herbicidal activity. The results are presented in Table A below.

Again following the procedure of Example 18, the compounds of Examples 25, 27 and 28 (compounds 2, 4, and 5) are tested for pre-emergence herbicidal activity. The results are given in Table A.

TABLE A

| | Average Herbicidal Activity, in % Control | | | |
|---|---|---|---|---|
| | Post | | Pre | |
| Compound | $GR^a$ | $BL^b$ | GR | BL |
| 2 | 96 | 100 | 95 | 100 |
| 3 | 83 | 100 | — | — |
| 4 | 100 | 100 | 100 | 100 |
| 5 | 81 | 100 | 100 | 100 |

$^a$GR = grasses
$^b$BL = broadleafs

EXAMPLE 30

Following the procedure of Example 18, the compound dimethylα-[2-nitro-5-(2-chloro-4-trifluoromethylphenoxy)phenoxy]ethylphosphonate is tested for pre-emergence and for post-emergence herbicidal activity. The average pre-emergence activity in grasses is 95% and in broadleafs, 100%. The post-emergence activity in both grasses and broadleafs is 100%.

EXAMPLE 31

Following the procedure of Example 22, the compounds of the following formula (VIII) listed under Table B are prepared.

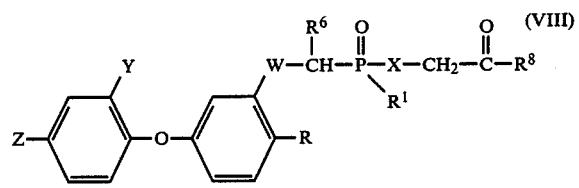

In the following Table B, it is understood that Z is trifluoromethyl, Y is chloro, $R^6$ is methyl, W is oxygen and X is oxygen in formula (VIII).

TABLE B

| Compound | R | $R^1$ | $R^8$ | m/s |
|---|---|---|---|---|
| 6 | $NO_2$ | —$CH_2CH_3$ | —O—$CH_2CH_2$—S—$CH_2CH_3$ | 599 |
| 7 | $NO_2$ | —$CH_2CH_3$ | —O—$CH_3$ | 525 |
| 8 | $NO_2$ | —$CH_3$ | —O—$CH_2CH_2$—O—$CH_3$ | 555 |
| 9 | Cl | —$CH_2CH_3$ | —O—$CH_3$ | 515 |
| 10 | $NO_2$ | —$CH_3$ | —O—$CH_2C\equiv CH$ | 535 |
| 11 | $NO_2$ | —$CH_2CH_3$ | —O—$CH_2C\equiv CH$ | 549 |
| 12 | $NO_2$ | —$CH_3$ | —O—$CH_2CH_2C(CH_3)_2$—O—$CH_3$ | 597 |
| 13 | $NO_2$ | —$CH_2CH_3$ | 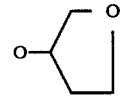 | 581 |
| 14 | $NO_2$ | —$CH_2CH_3$ | —$CH_3$ | 509 |

Compound 14 is prepared using the procedure of Example 22 by reaction of the phosphinic acid precursor with chloroacetone in acetone under reflux.

EXAMPLE 32

Using the procedures described herein, the compounds of formula (IX) listed under Table C are prepared wherein Z is trifluoromethyl, Y is chloro and W is oxygen.

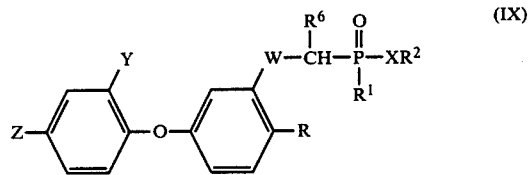

TABLE C

| Compound | R | $R^6$ | $R^1$ | $XR^2$ | m/s |
|---|---|---|---|---|---|
| 15 | $NO_2$ | $CH_3$ | $C_2H_5$ | $OC_2H_5$ | 481 |
| 16 | $NO_2$ | $CH_3$ | $C_2H_5$ | $OCH_3$ | 467 |
| 17 | Cl | $CH_3$ | $C_2H_5$ | $OC_2H_5$ | 471 |
| 18 | $NO_2$ | H | $CH_3$ | $OCH(CH_3)_2$ | 467 |
| 19 | $NO_2$ | H | $CH_3$ | $OCH_2CH_2$—S—$C_2H_5$ | 513 |
| 20 | $NO_2$ | $CH_3$ | $C_2H_5$ | $NH\,CH_3$ | 452 |
| 21 | $NO_2$ | H | $CH_3$ | $OCH_2CH(CH_3)_2$ | 481 |
| 22 | $NO_2$ | H | $CH_3$ | $OCH_2C\equiv CH$ | 463 |
| 23 | $NO_2$ | $CH_3$ | $C_2H_5$ | $OCH_2CH_2$—S—$C_2H_5$ | 541 |
| 24 | $NO_2$ | H | $CH_3$ | $OCH_2CH_2OCH_3$ | 483 |
| 25 | $NO_2$ | H | $CH_3$ | (tetrahydrofuran-O-) | 495 |

TABLE C-continued

| Compound | R | R⁶ | R¹ | XR² | m/s |
|---|---|---|---|---|---|
| 26 | NO₂ | CH₃ | C₂H₅ | 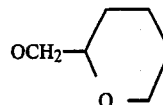 | 551 |
| 27 | NO₂ | H | CH₃ | 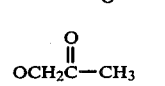 OCH₂C(O)—CH₃ | 481 |

Compounds 18 to 27 can be prepared by conversion of the phosphinic acid to the phosphinyl chloride using SOCl₂ followed by reaction with the appropriate alcohol or amine in a solvent such as CH₂Cl₂.

Compounds 15 and 17 can be prepared using the procedure of Example 19. Compound 16 can be prepared by the procedure of Example 21.

EXAMPLE 33

To a mixture of ethyl-P-ethylphosphite (20.4 g) and acetaldehyde (8.7 ml) is slowly added saturated sodium ethoxide until the internal temperature is raised to the maximum (about 100°). The reaction is then filtered through silica gel column to yield ethyl P-ethyl α-hydroxyethylphosphinate in good yield.

Using the procedure of Example 19, 9.2 g of the above phosphinate is reacted with mesyl chloride to yield ethyl P-ethyl α-mesyloxyethylphosphinate (9.1 g) which is reacted with 5-(2chloro-4-trifluoromethylphenoxy)-2-nitrophenol to yield ethyl P-ethyl-α-[2-nitrol-5-(2-chloro-4-trifluoromethylphenoxy)phenoxy]ethylphosphinate (Compound 15).

EXAMPLE 34

A mixture of P-ethyl-α-[2-nitro-5-(2-chloro-4-trifluoromethylphenoxy)phenoxy]ethylphosphinic acid (650 mg, 1.43 mm), α-bromoethyl acetate (430 mg), triethylamine (0.4 ml) and DMF (3.5 ml) is stirred at RT for 24 hours. The reaction product is taken up in CH₂Cl₂, washed, dried and concentrated under vacuum. The concentrate is purified by prep thin layer chromatography to yield 320 mg of the acetate (IX; Y is Cl, Z is CF₃, R is NO₂, W=X is O, R¹ is C₂H₅, R⁶ is CH₃, and R² is —CH(CH₃)—O—C(O)—CH₃) (Compound 28).

Using the above procedure, P-methyl-2-nitro-5(2chloro-4-trifluoromethylphenoxy)phenoxymethylphosphinic acid (0.5 g) is reacted with each of chloromethyl pivalate (265 mg) and α-bromoethyl acetate (354 mg) to give the respective pivalate (IX; R is NO₂, R¹ is CH₃, R⁶ is H, W=X is O, Y is Cl, Z is CF₃, R² is CH₂OC(O)C(CH₃)₃) in yield of 355 mg (Compound 29) and the acetate (IX; R is NO₂, R¹ is CH₃, R⁶ is H, W=X is O, Y is Cl, Z is CF₃, R² is CH(CH₃)OC(O)CH₃) in yield of 380 mg (Compound 30).

Using the above procedure, P-methyl-α-[2-nitro-5-(2-chloro-4-trifluoromethylphenoxy)phenoxy]ethylphosphinic acid (600 mg) is reacted with each of chloromethyl acetate (300 mg) and chloromethyl pivalate (0.3 ml, 2.18 mm) to give the respective acetate (IX; R is NO₂, R¹=R⁶ is CH₃, W—X is O, Y is Cl, Z is CF₃ and R² is CH₂OC(O)CH₃) in yield of 430 mg (Compound 31) and the pivalate (IX; R is NO₂, R¹=R⁶ is CH₃, W=X is O, Y is Cl, Z is CF₃ and R² is CH₂OC(O)C(CH₃)₃ in yield of 570 mg (Compound 32).

Following the test procedure of Example 18, each of the compounds listed in Table D is tested for pre- and post-emergence herbicidal activity with the result indicated in average percent control.

TABLE D

| Compound No. | Pre GR | Pre BL | Post GR | Post BL |
|---|---|---|---|---|
| 6 | 100 | 100 | 100 | 100 |
| 7 | 100 | 100 | 100 | 100 |
| 8 | 100 | 100 | 100 | 100 |
| 10 | 100 | 100 | 100 | 100 |
| 11 | 100 | 100 | 100 | 100 |
| 12 | 100 | 100 | 100 | 100 |
| 13 | 100 | 100 | 100 | 100 |
| 15 | 92 | 95 | 100 | 100 |
| 18 | 87 | 99 | 97 | 100 |
| 19 | 100 | 100 | 80 | 100 |
| 22 | 98 | 98 | 98 | 100 |
| 24 | 99 | 98 | 99 | 99 |
| 25 | 99 | 99 | 100 | 100 |
| 29 | 98 | 100 | 98 | 100 |
| 30 | 100 | 96 | 98 | 100 |

The herbicidal activity of the compounds listed in Table E is indicated in average percent control for pre-emergence applicaton at the rate of 3.3 lbs/acre.

TABLE E

| Compound No. | GR | BL |
|---|---|---|
| 4 | 100 | 100 |
| 7 | 100 | 100 |
| 16 | 90 | 94 |
| 28 | 100 | 92 |

Post-emergence application of the compounds listed in Table F on broadleafs at the rate of 0.33 lbs/acres resulted in the average percent control indicated.

TABLE F

| Compound No. | BL |
|---|---|
| 4 | 100 |
| 7 | 100 |
| 15 | 87 |
| 28 | 100 |
| 29 | 100 |
| 30 | 98 |

Emulsifiable concentrate of compound 7 or other compound of formula (A) of the present invention is prepared as follows (ingredients in percent by weight).

| Compound No. 7 | 27.8 |
|---|---|
| Xylene | 62.2 |
| Toximol S | 5.0 |
| Atlox 8916 TF | 5.0 |

Toximol is an emulsifier of Stepan Chemical Company. Atlox 8916 TF is an emulsifier of ICI Americas, Inc.

Flowable formulation is prepared as follows using Compound 28 (or other compound of formula (A));

| (1) Compound 28 | 3.00 |
|---|---|
| Toximol 360A | 3.00 |
| Sun 7N (oil) | 30.00 |
| (2) Water | 60.85 |
| Gelvatol 20/30 | 3.00 |
| Kelzan | 0.15 |

Premix (1) is dispersed in high speed blender and then premix (2) is added and stirring continued for about 5 minutes.

The crops rice, wheat and barley show excellent tolerance to pre-emergent application of the compounds of the present invention such as compound no. 7. The compounds of the present invention are useful for the control of weeds in rice when the compound is introduced into the floodwater.

EXAMPLE 35

Using the procedure of Example 19, 3-(2-chloro-4-tri-fluoromethylphenoxy)phenol is reacted with ethyl P-methyl-α-mesyloxyethylphosphinate to yield ethyl P-methyl-α-[3-2-chloro-4-trifluoromethylphenoxy)]ethylphosphinate (IX; R is H, $R^1=R^6$ is $CH_3$, W=X is O, $R^2$ is $C_2H_5$, Y is Cl, Z is $CF_3$).

The compounds of formula (A) of the present invention can be prepared according to the following outlined method in addition to the preparations described hereinabove.

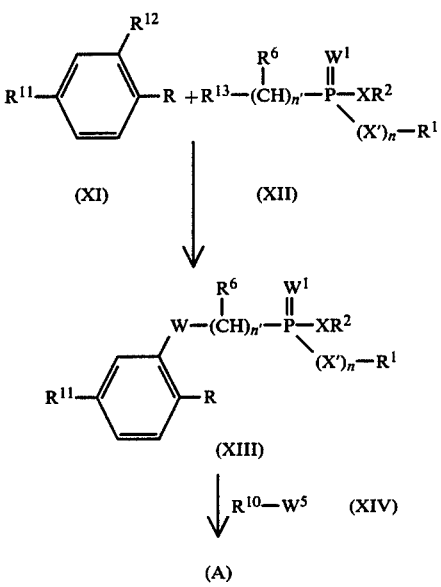

In the above formulas (XI) and (XII), when $R^{12}$ is nitro, bromo or chloro and $R^{13}$ is hydroxy, thiol or $NR^5$, then R is nitro and when $R^{12}$ is hydroxy or thiol and $R^{13}$ is bromo, chloro, iodo, mesyloxy or tosyloxy, then R is nitro, chloro, hydrogen or cyano. $W^5$ is bromo, chloro, iodo, hydroxy or thiol.

In the practice of the above outlined process, a benzene compound of formula (XI) is reacted with a phosphinate or phosphonate of formula (XII) using conditions such as described in Examples 1, 19 and 24 to yield a compound of formula (XIII) which is then reacted with a halide, alcohol or thiol of formula (XIV), according to the value of $R^{11}$, to prepare a compound of formula (A) wherein $W^2$ is oxygen or sulfur.

EXAMPLE 36

(A) A mixture of 5-chloro-2-nitrophenol (3.3 mmol), ethyl P-methyl α-mesyloxyethylphosphinate (5.2 mmol), potassium carbonate (1.5 eq.) and 2-butanone (30 ml) is heated under reflux for about 30 hours. The reaction is worked up as in Example 19 to yield ethyl P-methyl α-(2-nitro-5-chlorophenoxy) ethyl phosphinate (XIII: R is $NO_2$, $R^1=R^6$ is $CH_3$, W=$W^1$=X is O, n' is 1, $R^{11}$ is Cl, n is zero).

(B) The phosphinate of part (A) is reacted with 2-chloro-4-trifluoromethylphenol in the presence of base using the procedure of U.S. Pat. Nos. 3,784,635 or 4,277,624 to give ethyl P-methyl-α-[2-nitro-5-(2-chloro-4-trifluoromethylphenoxy)phenoxy]ethylphosphinate.

EXAMPLE 37

(A) a mixture of 3,4-dinitrophenol (3 mmol), diethyl α-hydroxyethylphosphonate (5 mmol), potassium carbonate (1.8 eq) and 2-butanone (15 ml) is heated under reflux for about 24 hours. The reaction is worked up as in Example 24 to give diethyl α-(2-nitro-5-hydroxyphenoxy)ethyl phosphonate (XIII; R is $NO_2$, $R^1=R^2$ is $C_2H_5$, $R^6$ is $CH_3$, n'=n is 1, W=$W^1$=X—X' is O, $R^{11}$ is OH).

(B) The phosphonate of part A is reacted with 2-chloro-5-trifluoromethylpyridine in the presence of base using the procedure of U.S. Pat. No. 4,326,880 to yield diethyl α-[2-nitro-5O(5-trifluoromethyl-2-pyridyloxy)phenoxy]ethylphosphonate.

EXAMPLE 38

The compound of Example 35 is nitrated using $HNO_3/H_2SO_4$ following the process of U.S. Pat. No. 4,326,880 to yield the corresponding 2-nitro derivative (IX; R is $NO_2$, $R^5=R^6$ is $CH_3$, W=X is O, $R^2$ is $C_2H_5$, Y is Cl, Z is $CF_3$).

EXAMPLE 39

The process of Example 36 is repeated using each of 3,4-dinitrophenol, 5-chloro-1,2-dinitrobenzene, 2,5-dichloronitrobenzene, 2-nitro-5-thiolchlorobenzene and 3-chloro-4-nitrophenol in place of 5-chloro-2-nitrophenol to yield the following phosphinates.

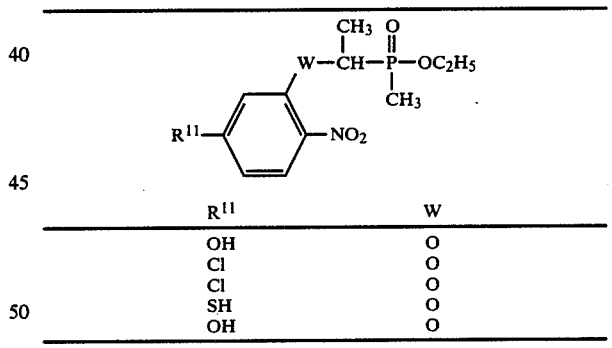

| $R^{11}$ | W |
|---|---|
| OH | O |
| Cl | O |
| Cl | O |
| SH | O |
| OH | O |

What is claimed is:

1. A compound of the formula (XIII):

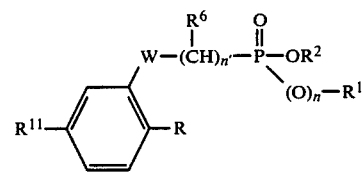

wherein,
W is oxygen or sulfur;
n' is 1, 2 or 3;
n is 0 or 1;
R is nitro, or cyano;

$R^1$ is lower alkyl;
$R^2$ is lower alkyl;
$R^6$ is hydrogen or lower alkyl; and
$R^{11}$ is bromo, chloro or hydroxy.

2. A compound according to claim 1 wherein $R^{11}$ is chloro, R is nitro, W is oxygen and $R^6$ is hydrogen or methyl.

3. A compound according to claim 2 wherein n' is one, n is zero and $R^1$ is methyl or ethyl.

* * * * *